United States Patent
Roussouly et al.

(10) Patent No.: US 7,322,980 B2
(45) Date of Patent: Jan. 29, 2008

(54) ANTERIOR SPINAL ANCHOR PLATE

(75) Inventors: Pierre Roussouly, Saint Cyr Au Mont d'Or (FR); Daniel Chopin, Groffliers (FR); Laure Bruneau, Paris (FR); Philippe Lemaitre, Alfortville (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 576 days.

(21) Appl. No.: 10/375,850

(22) Filed: Feb. 26, 2003

(65) Prior Publication Data

US 2004/0059332 A1    Mar. 25, 2004

(30) Foreign Application Priority Data

Feb. 27, 2002   (FR)   .................................. 02 02490

(51) Int. Cl.
*A61B 17/56*   (2006.01)
(52) U.S. Cl. ....................................................... 606/61
(58) Field of Classification Search ............ 606/69–71, 606/61
See application file for complete search history.

(56) References Cited

U.S. PATENT DOCUMENTS

| 4,747,204 | A | * | 5/1988 | Pratt et al. ..................... 29/523 |
| 5,364,399 | A | * | 11/1994 | Lowery et al. ................ 606/69 |
| 5,702,395 | A | | 12/1997 | Hopf |
| 5,728,097 | A | | 3/1998 | Mathews |
| 6,214,005 | B1 | | 4/2001 | Benzel et al. |
| 6,214,006 | B1 | | 4/2001 | Metz-Stavenhagen |
| 6,248,104 | B1 | | 6/2001 | Chopin et al. |
| 6,355,039 | B1 | * | 3/2002 | Troussel et al. ............... 606/61 |
| 6,746,450 | B1 | * | 6/2004 | Wall et al. ..................... 606/61 |
| 2001/0047174 | A1 | | 11/2001 | Donno et al. |
| 2002/0019633 | A1 | | 2/2002 | Ray |

FOREIGN PATENT DOCUMENTS

| EP | 0 574 099 A2 | 6/1992 |
| FR | 2 697 744 A1 | 11/1992 |
| FR | 2 784 571 A1 | 10/1998 |
| FR | A-2 761 256 | 10/1998 |

OTHER PUBLICATIONS

Medtronic Sofamor Danek, "Colorado 2 The New Revolution—Surgical Technique", © Apr. 2000.
Medtronic Sofamor Danek, "Colorado 2 The New Revolution—Posterior & Anterior Spinal System (Deformities, Degenerative, Trauma, Tumor)", © Dec. 1998.

* cited by examiner

*Primary Examiner*—Eduardo C. Robert
*Assistant Examiner*—Michael J. Araj
(74) *Attorney, Agent, or Firm*—Woodard, Emhardt, Moriarty, McNett & Henry LLP

(57) ABSTRACT

Anchoring plate for a device for osteosynthesis of the vertebral column, including means for connecting it to one or more rods or to a plate. Its lower face is configured to match the shape of a contact zone situated to straddle two vertebrae, and it has openings for the passage of screws. The device for osteosynthesis of the vertebral column includes one or more rods or plates connected to vertebrae by way of connectors and anchoring plates. At least one of the anchoring plates is of the above type described above.

17 Claims, 3 Drawing Sheets

ANTERIOR SPINAL ANCHOR PLATE

REFERENCE TO RELATED APPLICATIONS

The present application claims the benefit of French Patent Application No. 02 02490 filed Feb. 27, 2002, which is hereby incorporated by reference in its entirety.

BACKGROUND

The invention generally relates to the field of prostheses for the vertebral column, which are intended to correct and stabilize scoliosis or to reposition and stabilize vertebrae in the case of a trauma or a tumor.

Such prostheses, called spinal osteosynthesis devices, can be implanted either by the posterior route or by the anterior route. When a posterior route or approach is used, the surgeon is unable to directly access the vertebral bodies. In contrast, the anterior route has in particular the characteristic of permitting direct access to the vertebral bodies, as well as many other advantages which are listed in the document FR-A-2 697 744, which is hereby incorporated by reference in its entirety.

Such devices implanted by the anterior route and permitting fusion between two or more adjacent vertebrae can be classified in two categories:
- those which use one or more components in the form of rigid plates or the like, the plates being fixed to the different vertebrae in the zone to be treated;
- those which use one or two metal rods fixed along the vertebral column by means of suitable connection devices.

To fix these devices on the vertebral column using the known techniques, the surgeon fixes, on each vertebra of the zone in question, a plate-like anchoring member, called an anchoring plate, which serves as an anchoring point for the component or components for regulating the relative positions of these vertebrae, namely the plates and/or the rods.

Generally, the anchoring plate is placed in an orientation that is substantially parallel to the vertebral discs, and its lower face must be quite strongly curved inwards to best match the surface of the vertebra in this orientation. In the case where plates are used, these are directly fixed on the anchoring plate. In the case where rods are used, these are generally connected to the anchoring plate via one or more connectors that can each connect a single rod to the anchoring plate (as in FR-A-2 761 256), or two rods simultaneously (as in FR-A-2 697 744).

In order for the existing devices to be implanted in the thoracic region, it is necessary for the surgeon to make an incision between two ribs. In some cases the surgeon is forced to section a rib. However, as the available space is relatively small, the surgeon then has few possibilities for fixing another anchoring plate on an adjacent vertebra. Therefore, in order to do this, the surgeon very often has to make a new incision, with all the disadvantages which this means for the patient.

SUMMARY

One object of the present invention is to provide unique instrumentation for spinal osteosynthesis.

Another object of the present invention is to provide a unique anchoring plate and corresponding method to facilitate implantation of spinal osteosynthesis apparatus.

To this end, one embodiment of the invention is an anchoring plate for a device for osteosynthesis of the vertebral column, of the type comprising means for connecting it to one or more rods or plates, characterized in that its lower face is configured to match the shape of a contact zone that is situated to straddle two vertebrae, and in that it has openings for the passage of screws intended to be implanted in the vertebrae.

The anchoring plate can have straight side edges connected via its lower face which has a concavity about the longitudinal axis of the plate.

The means for connecting the anchoring plate to one or more rods of the osteosynthesis device can comprise a threaded rod formed integrally with the anchoring plate or fixed to it, and intended to receive a connector and a nut for immobilizing the rod of the osteosynthesis device in the connector.

The invention also relates to a device for osteosynthesis of the vertebral column, of the type comprising one or more rods or plates intended to be connected to vertebrae by way of connectors and anchoring plates fixed on the vertebrae, characterized in that at least one of the anchoring plates is of the above type.

The anchoring plate of the above type and the corresponding connector can be configured in such a way that the face of the connector directed towards the plate comes into contact with the screws.

As will have been appreciated, in one form, the invention concerns an anchoring plate which is no longer fixed on a single vertebra but simultaneously on two adjacent vertebrae.

Further objects, embodiments, forms, aspects, features, benefits, and/or advantages will be apparent from the description and drawings provided herewith.

BRIEF DESCRIPTION OF DRAWINGS

The invention will be better understood on reading the description which follows and in which reference is made to the following attached figures.

DESCRIPTION OF SELECTED EMBODIMENTS

Figure 1:
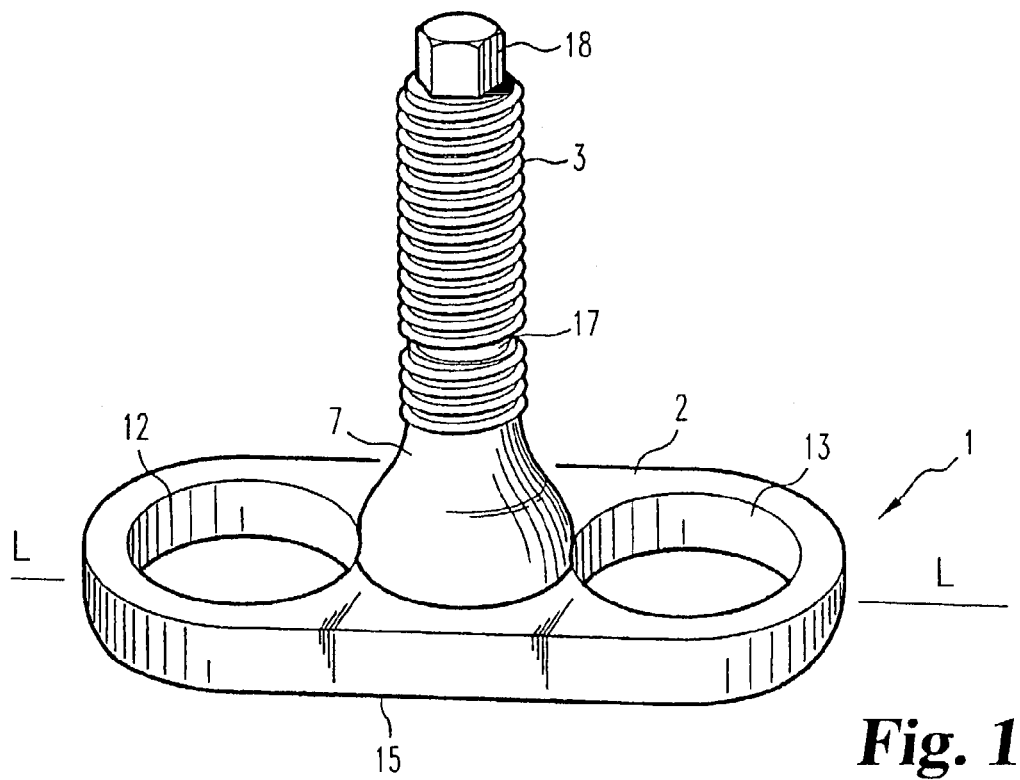
FIG. 1 shows a perspective view of an anchoring plate according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated device, and further applications of the principles of the invention as illustrated or described herein are contemplated as would normally occur to one skilled in the art to which the invention relates.

Figure 2:
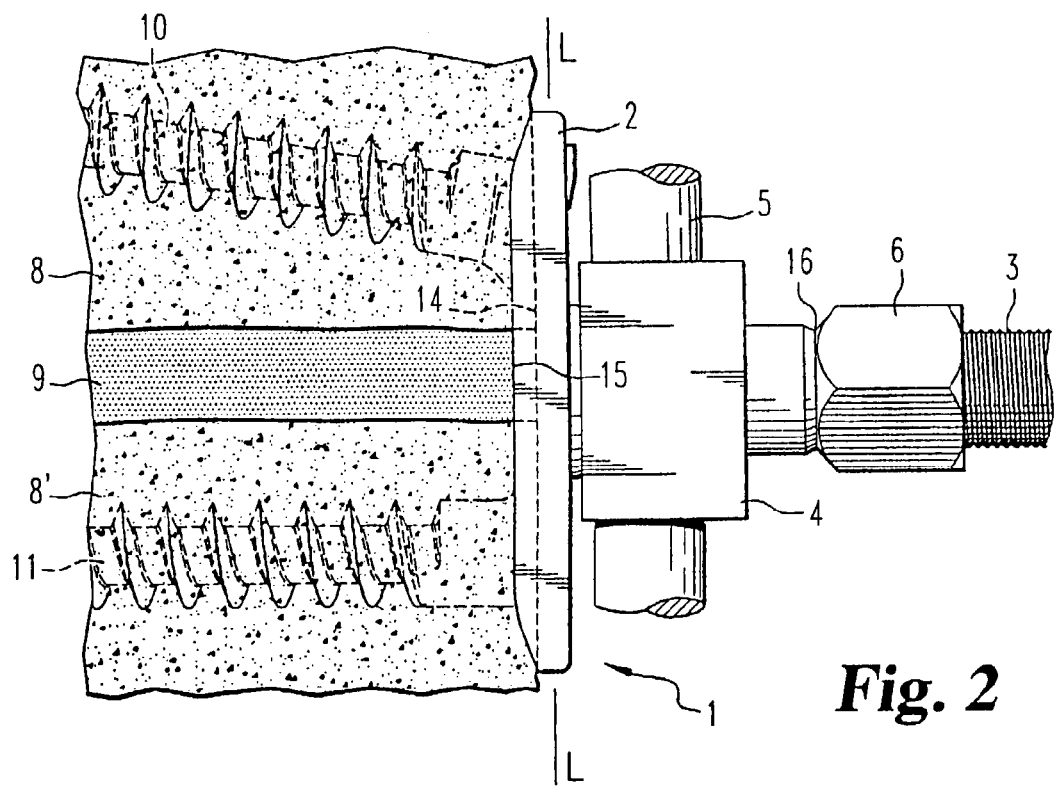
FIG. 2 shows a partial, cross-sectional view of the FIG. 1 plate implanted on two adjacent vertebrae and provided with a connector which connects it to a rod of a spinal osteosynthesis device.
Figure 5:
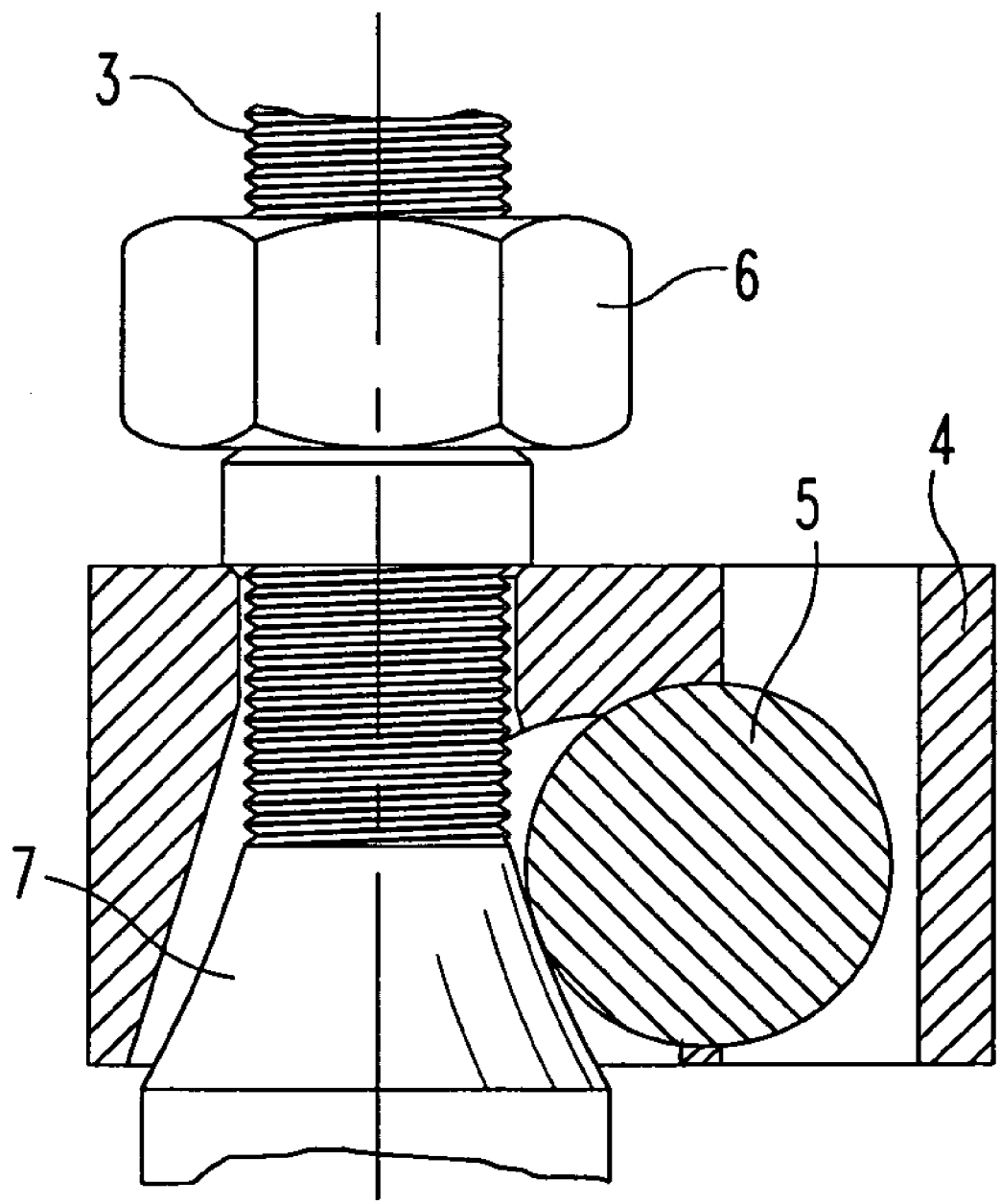
FIG. 5 shows a partial, cross-sectional view of the connector engaging the rod for the FIG. 1 anchoring plate.

An example of an anchoring plate 1 according to one embodiment of the present invention, which is shown in isolation in FIG. 1 and in position in FIG. 2, includes a base plate 2 and attachment means for connecting it to one or two rods of the spinal osteosynthesis device with which it is to be connected. In the example shown, these attachment means are formed by a threaded rod or stem 3 which extends substantially perpendicular to the base plate 2, on which there will be fitted a connector 4 in which a rod 5 of the spinal osteosynthesis device will be inserted. In one form, the connector 4 is of the type as described in the document FR-A-2 761 256, which is hereby incorporated by reference in its entirety (FIG.5). The rod 5 is immobilized in the connector 4 by tightening a nut 6, which is engaged on the thread of the stem 3. This nut 6 exerts a pressure on the connector 4 in such a way as to cause it to transmit this pressure to the rod 5 and wedge it against a conical support 7 formed at the base of the stem 3. In the illustrated embodiment, the stem 3 is threaded, but it is contemplated that in other embodiments that the stem 3 can be unthreaded.

It must be emphasized that the connector 4 described and shown in FIG. 2 is a nonlimiting example only and that it could have a different configuration. In particular, as in document FR-A-2 697 744, it could permit connection of two rods to the anchoring plate 1.

The threaded stem 3 in the example shown is an integral part of the plate 1, but the stem 3 could be an element independent of the anchoring plate 1 and able to be fixed to the anchoring plate 1, for example by a threaded connection.

The anchor plate 1 is configured to be attached to the spine from an anterior approach. To fit the spinal osteosynthesis device incorporating the anchoring plates 1 according to one embodiment, the surgeon begins by fixing each of the anchoring plates 1 on a pair of vertebrae 8, 8' which are separated by a disc 9 or a bone graft if the patient has undergone. partial or total discectomy. This fixing is done using two screws 10, 11 which pass through corresponding openings 12, 13 formed in the anchoring plate 1. As shown in FIGS. 1 and 2, the openings 12, 13 are positioned along longitudinal axis L of the base plate 2, which extends along the vertebrae 8, 8' when the anchoring plate is attached. As depicted, the longitudinal axis L of the base plate 2 extends across the disc 9 in a transverse manner, such that in one form the base plate 2 is oriented substantially perpendicular to disc 9. In the illustrated embodiment, the stem 3 is positioned between the openings 12, 13 along the longitudinal axis L. In one form, the openings 12, 13 and the heads of the screws 10, 11 are configured in such a way as to give the screws 10, 11 diverging orientations after they have been secured. The diverging screw orientations permits more stable anchoring than if these screw orientations were parallel. However, the surgeon can be allowed to choose, without restriction, the orientation to give to each of the screws 10, 11 by providing them with spherical heads which cooperate with corresponding spherical supports formed on the walls defining the openings 12, 13 of the anchoring plate 1.

Lower engagement face 14 of the anchoring plate 1 is configured so as to correspond to the shape of the vertebrae 8, 8' at a contact zone where the anchoring plate 1 is attached.

Figure 3:
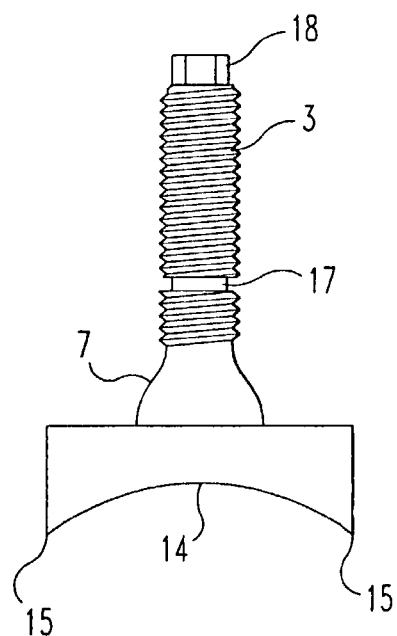
FIG. 3 shows an end view of the FIG. 1 plate.

Compared to the known anchoring plates intended to be fixed on one vertebra only, the lower face 14 has a shape, which is generally much less inwardly curved. As shown in FIGS. 1, the plate 1 has straight side edges 15 that extend along the longitudinal axis L of the base plate 2. With reference to FIG. 3, the side edges 15 are connected together via the lower engagement face 14, which is slightly concave about the longitudinal axis L of the plate 1. As should be appreciated, having the lower face 14 curved in such a manner makes the anchoring plate 1 well-suited for attaching to both of the vertebrae 8, 8' from an anterior approach.

As noted above, the anchoring plate 1 is attached to the vertebrae 8, 8' from an anterior approach. During fixation, an instrument can be used to hold the anchoring plate 1 by the stem 3. With the stem 3, the surgeon can press the anchoring plate 1 against the vertebrae 8, 8'. After the anchoring plates 1 have been secured, the connectors 4, in which the rod 5 has previously been placed (or two such rods 5 if the connector 4 is designed to receive two of them) are engaged on the stem 3. The assembly is then joined together by tightening nut 6 on the stem 3. In the illustrated embodiment, the nut 6 is divided in two parts along a groove 16. When a predetermined rupture torque is reached, the nut 6 splits along groove 16 so that the nut 6 is not over tightened. Likewise, a break off groove 17 is formed on the stem 3 of the anchoring plate 1. Once the rod 5 is fitted, torque can be applied to the stem 3 by twisting its end 18. End 18 is shaped to engage an instrument such as a screwdriver or the like. When a predetermined torque is applied to end 18, the stem 3 breaks along groove 17. By splitting the nut 6 and stem 3 along grooves 16 and 17, respectively, the space taken up by the osteosynthesis device after fitting is reduced.

Figure 4:
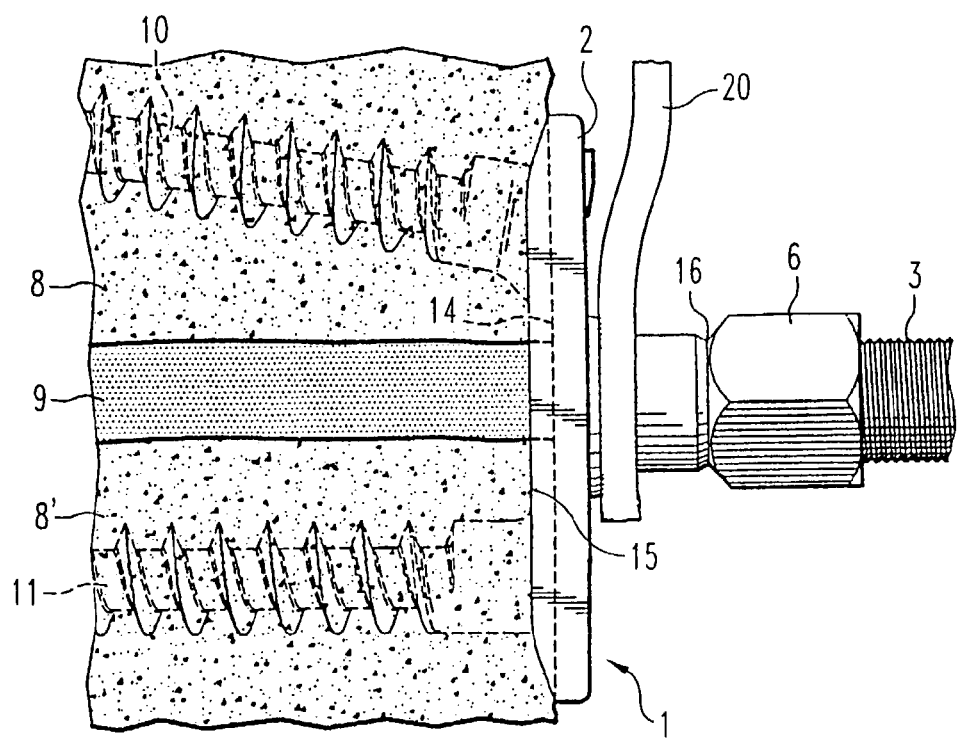
FIG. 4 shows a cross-sectional view of the FIG. 1 plate securing a connection plate to two adjacent vertebrae.

As depicted in FIG. 2, the connector 4 and the anchoring plate 1 can be configured in such a way that when the connector 4 is in place and fixed by the nut 6, the face of the connector 4 is directed towards the plate 1 comes into contact with or near to the heads of the screws 10, 11 so as to at least partially cover the openings 12, 13, thereby minimizing the risk of the screws 10, 11 backing out. As should be appreciated, the anchoring plate 1 can be used in other type of vertebrae anchoring systems. For example, as illustrated in FIG. 4, the anchoring plate 1 is not connected to a rod 5 by way of a connector 4, but to an end of a plate 20 (or several plates), of which the other end of the plate 20 is connected to another anchoring plate, which can be similar to the anchoring plate 1 according to the present invention. It is contemplated other types of connection members, besides rods 5 and plates 20, can be used to couple the anchoring plates 1 together.

Compared to the previously known anchoring plates which could be fixed on only one vertebra at a time, the anchoring plates 1 according to the present invention make it possible to minimize the number of plates that need to be fitted. By reducing the number of anchoring plates required, the number of incisions in the patient that are needed for implanting the osteosynthesis system are reduced, in particular when the osteosynthesis system extends along a substantial length of the vertebral column. It is thus possible to minimize the trauma experienced by the patient, the time needed for implanting the device, and the number of components used. Moreover, since the anchoring plates 1 are secured across at least two vertebrae 8, 8', the anchoring plates 1 can be firmly secured on vertebrae that have a relatively small size, such as the upper thoracic vertebrae. Other types anchoring plates can of course be used in conjunction with the anchoring plates 1 according to the present invention. For example, one or more anchoring plates that are configured to secure to just one vertebra can be incorporated into an osteosynthesis system that further includes at least one anchoring plate 1 according to the present invention, which is secured across two vertebrae.

While the invention has been illustrated and described in detail in the drawings and foregoing description, the same is to be considered as illustrative and not restrictive in character, it being understood that only the preferred embodiment has been shown and described and that all changes, modifications, and equivalents that come within the spirit of the inventions described herein and/or defined by the following claims are desired to be protected.

What is claimed is:

1. An osteosynthesis system for securing to adjacent first and second vertebrae, comprising:
   a first base plate defining a first opening adapted to receive a first vertebral engagement member for securing said first base plate to the first vertebra and a second opening adapted to receive a second vertebral engagement member for securing said first base plate to the second vertebra, said first base plate having a longitudinal axis that extends along the first and second vertebrae when said first base plate is secured to the first and second vertebrae;
   a connection member configured to secure said first base plate to a second base plate;
   a stem extending from said first base plate adapted to secure said connection member to said first base plate;
   a nut securing said connection member to said stem;
   wherein said first base plate has a vertebrae engagement surface adapted to engage the first and second vertebrae, said vertebrae engagement surface being concave along said longitudinal axis to conform with the first and second vertebrae;
   wherein said first vertebral engagement member includes a first screw;
   wherein said second vertebral engagement member includes a second screw; and
   wherein the first opening and the second opening are configured to give the first screw and the second screw a diverging orientation to enhance anchoring stability.

2. The system of claim 1, wherein said first base plate has straight side edges extending parallel to said longitudinal axis that are connected via said vertebrae engagement surface.

3. The system of claim 1, wherein said connection member includes a connecting rod and a connector engaging said connecting rod.

4. The system of claim 3, further comprising:
   said first vertebral engagement member engaging said first vertebra;
   said second vertebral engagement member engaging said second vertebra; and
   wherein said connector is oriented on said stem to at least partially cover said first opening and said second opening to minimize chances of said first screw and said second screw from backing out.

5. The system of claim 3, wherein the stem includes a conical support against which the rod is wedged.

6. The system of claim 1, wherein said connection member includes a connecting plate.

7. The system of claim 1, wherein said stem is positioned between said first opening and said second opening.

8. The system of claim 1, wherein the nut includes a groove that is configured to rupture at a predetermined rupture torque to prevent over tightening.

9. The system of claim 1, wherein the stem includes a break off groove configured to rupture at a predetermined torque to reduce the space occupied by the first base plate.

10. An osteosynthesis system for securing to adjacent first and second vertebrae, comprising:
    a first base plate defining a first opening adapted to receive a first vertebral engagement member for securing said first base plate to the first vertebra and a second opening adapted to receive a second vertebral engagement member for securing said first base plate to the second vertebra, said first base plate having a longitudinal axis that extends along the first and second vertebrae when said first base plate is secured to the first and second vertebrae;
    a connection member configured to secure said first base plate to a second base plate;
    a stem extending from said first base plate adapted to secure said connection member to said first base plate;
    a nut securing said connection member to said stem;
    wherein said first base plate has a vertebrae engagement surface adapted to engage the first and second vertebrae, said vertebrae engagement surface being concave along said longitudinal axis to conform with the first and second vertebrae; and
    wherein the nut includes a groove that is configured to rupture at a predetermined rupture torque to prevent over tightening.

11. The system of claim 10, wherein said connection member includes a connecting rod and a connector engaging said connecting rod.

12. The system of claim 11, further comprising:
    said first vertebral engagement member engaging said first vertebra, wherein said first vertebral engagement member includes a first screw;
    said second vertebral engagement member engaging said second vertebra, wherein said second vertebral engagement member includes a second screw;
    wherein said connector is oriented on said stem to at least partially cover said first opening and said second opening to minimize chances of said first screw and said second screw from backing out.

13. The system of claim 11, wherein the stem includes a conical support against which the rod is wedged.

14. The system of claim 10, wherein said connection member includes a connecting plate.

15. The system of claim 10, wherein the stem includes a break off groove configured to rupture at a predetermined torque to reduce the space occupied by the first base plate.

16. An osteosynthesis system for securing to adjacent first and second vertebrae, comprising:
    a first base plate defining a first opening adapted to receive a first vertebral engagement member for securing said first base plate to the first vertebra and a second opening adapted to receive a second vertebral engagement member for securing said first base plate to the second vertebra, said first base plate having a longitudinal axis that extends along the first and second vertebrae when said first base plate is secured to the first and second vertebrae;
    a connection member configured to secure said first base plate to a second base plate;
    a stem extending from said first base plate adapted to secure said connection member to said first base plate;
    a nut securing said connection member to said stem;
    wherein said first base plate has a vertebrae engagement surface adapted to engage the first and second vertebrae, said vertebrae engagement surface being concave along said longitudinal axis to conform with the first and second vertebrae;
    wherein the stem includes a break off groove configured to rupture at a predetermined torque to reduce the space occupied by the first base plate;
    wherein said connection member includes a connecting rod and a connector engaging said connecting rod; and
    wherein the stem includes a conical support against which the rod is wedged.

17. The system of claim 16, further comprising:
said first vertebral engagement member engaging said first vertebra, wherein said first vertebral engagement member includes a first screw;
said second vertebral engagement member engaging said second vertebra, wherein said second vertebral engagement member includes a second screw;
wherein said connector is oriented on said stem to at least partially cover said first opening and said second opening to minimize chances of said first screw and said second screw from backing out.

* * * * *